United States Patent
Shiao

(10) Patent No.: US 11,944,417 B2
(45) Date of Patent: Apr. 2, 2024

(54) WEARING DETECTION METHOD, WEARABLE DEVICE, AND COMPUTER READABLE STORAGE MEDIUM

(71) Applicant: BOMDIC INC., New Taipei (TW)

(72) Inventor: Yao Shiao, New Taipei (TW)

(73) Assignee: BOMDIC INC., New Taipei (TW)

( * ) Notice: Subject to any disclaimer, the term of this patent is extended or adjusted under 35 U.S.C. 154(b) by 280 days.

(21) Appl. No.: 17/562,000

(22) Filed: Dec. 27, 2021

(65) Prior Publication Data

US 2023/0200671 A1   Jun. 29, 2023

(51) Int. Cl.
*A61B 5/024*   (2006.01)
*A61B 5/00*   (2006.01)
*G16H 40/67*   (2018.01)

(52) U.S. Cl.
CPC ...... *A61B 5/02438* (2013.01); *A61B 5/02416* (2013.01); *A61B 5/7285* (2013.01); *G16H 40/67* (2018.01); *A61B 2560/0209* (2013.01); *A61B 2562/0219* (2013.01)

(58) Field of Classification Search
CPC .................. A61B 5/681; A61B 5/7285; A61B 2562/0219
See application file for complete search history.

(56) References Cited

U.S. PATENT DOCUMENTS

| 2012/0029363 | A1* | 2/2012 | Lund | A61B 5/6826 |
| | | | | 600/485 |
| 2021/0110019 | A1* | 4/2021 | Ko | G06F 1/1684 |
| 2021/0386310 | A1 | 12/2021 | Hong et al. | |
| 2022/0133241 | A1* | 5/2022 | Jones | A61B 5/02108 |
| | | | | 600/485 |

FOREIGN PATENT DOCUMENTS

| CN | 107822607 | 3/2018 |
| CN | 109077710 | 12/2018 |
| CN | 105425940 | 12/2019 |
| CN | 112165897 | 1/2021 |
| TW | 201918222 | 5/2019 |
| WO | 2018209829 | 11/2018 |

OTHER PUBLICATIONS

"Office Action of Taiwan Counterpart Application", dated Aug. 4, 2022, p. 1-p. 10.

* cited by examiner

*Primary Examiner* — Gerald Johnson
(74) *Attorney, Agent, or Firm* — JCIPRNET

(57) ABSTRACT

The disclosure provides a wearing detection method, a wearable device, and a computer readable storage medium. The method includes: in response to determining that the wearable device is in a static state, emitting a plurality of first photoplethysmography (PPG) signals, and detecting a plurality of second PPG signals corresponding to the first PPG signals; obtaining a zero-crossing rate corresponding to the second PPG signals; and in response to determining that the zero-crossing rate of the second PPG signals is higher than a reference threshold, determining that the wearable device is in an unworn state.

19 Claims, 8 Drawing Sheets

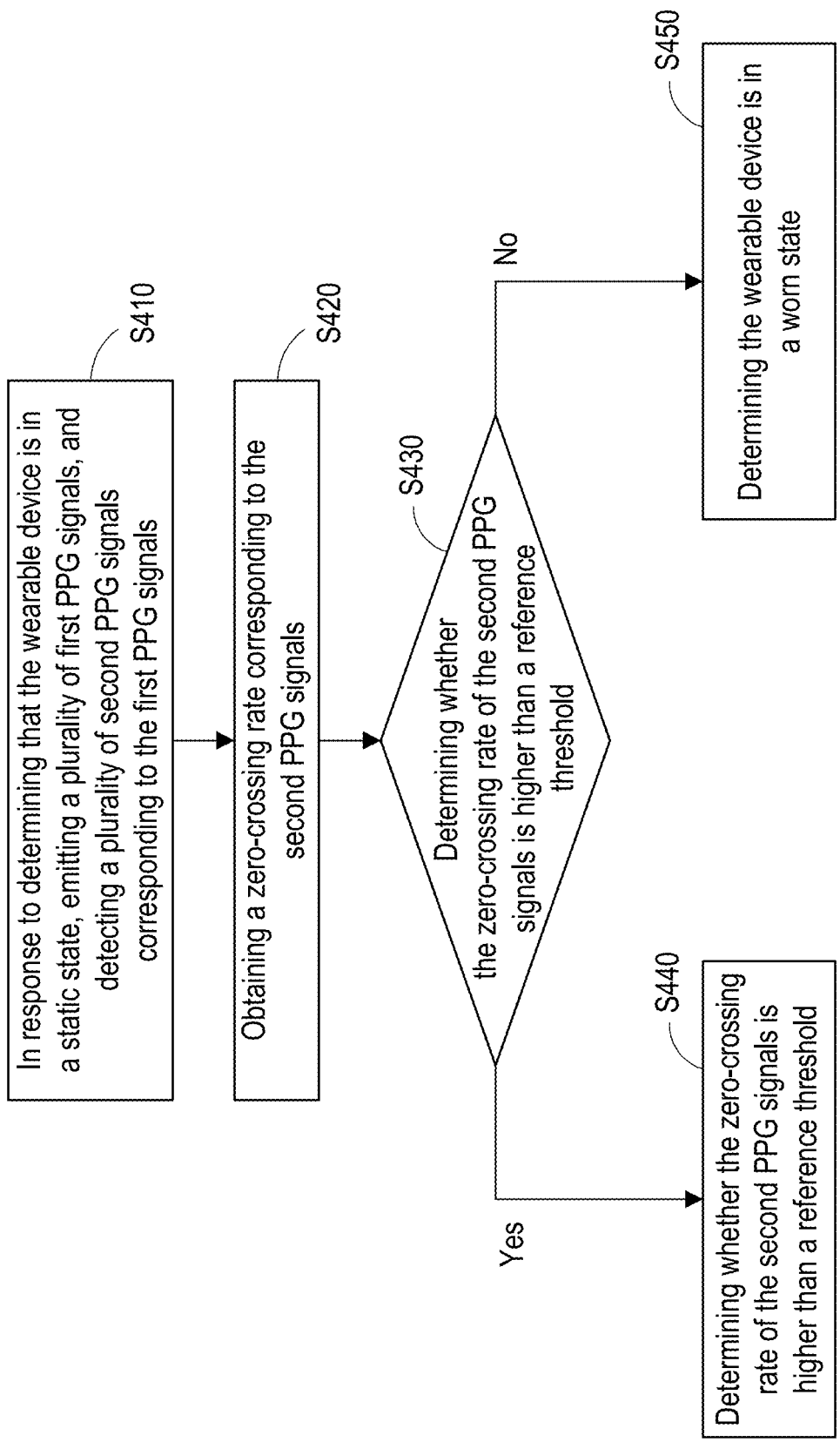

WEARING DETECTION METHOD, WEARABLE DEVICE, AND COMPUTER READABLE STORAGE MEDIUM

BACKGROUND

Technical Field

The disclosure relates to a wearing detection mechanism, and in particular to a wearing detection method, wearable device and computer-readable storage medium that can detect whether a wearable device is in a worn state or an unworn state.

Description of Related Art

Generally, wearable devices are often provided with detection elements dedicated to detecting whether the wearable device is being worn by a user. For example, a proximity sensor (such as an infrared transceiver circuit) of a smart watch may be disposed on a surface in contact with the user to specifically detect whether the smart watch is being worn on the user's body. However, such a specific proximity sensor not only occupies a part of the space on a wearable device but also increases the power consumption and implementation cost of the wearable device.

Therefore, for those skilled in the art, it is an important issue that how to design a mechanism which can accurately detect whether the wearable device is being worn by the user without setting up a dedicated proximity sensor on the wearable device for power consumption and implementation cost.

SUMMARY

In view of this, the application provides a wearing detection method, a wearable device, and a computer readable storage medium, which can be used to solve the technical problems.

The application provides a wearing detection method adapted for a wearable device includes: in response to determining that the wearable device is in a static state, emitting a plurality of first photoplethysmography (PPG) signals, and detecting a plurality of second PPG signals corresponding to the first PPG signals; obtaining a zero-crossing rate corresponding to the second PPG signals; and in response to determining that the zero-crossing rate of the second PPG signals is greater than a reference threshold, determining that the wearable device is in an unworn state.

The application provides a wearable device, and the wearable device includes a PPG signal transceiver and a processor. The processor is coupled to the PPG signal transceiver. In response to determining that the wearable device is in a static state by the processor, the processor controls the PPG signal transceiver to emit a plurality of first PPG signals and detect a plurality of second PPG signals corresponding to the first PPG signals. The processor obtains a zero-crossing rate corresponding to the second PPG signals. In response to determining that the zero-crossing rate of the second PPG signals is greater than a reference threshold by the processor, the processor determines that the wearable device is in an unworn state.

The application provides a computer readable storage medium, and the computer readable storage medium records an executable computer program that is loaded by a wearable device to perform the following steps: in response to determining that the wearable device is in a static state, emitting a plurality of first photoplethysmography (PPG) signals, and detecting a plurality of second PPG signals corresponding to the first PPG signals; obtaining a zero-crossing rate corresponding to the second PPG signals; in response to determining that the zero-crossing rate of the second PPG signals is greater than a reference threshold, determining that the wearable device is in an unworn state; in response to determining that the zero-crossing rate of the second PPG signals is not greater than the reference threshold, determining that the wearable device is in a worn state.

BRIEF DESCRIPTION OF THE DRAWINGS

FIG. 4 is a flowchart of a wearing detection method according to an embodiment of the application.

DESCRIPTION OF THE EMBODIMENTS

Figure 1:
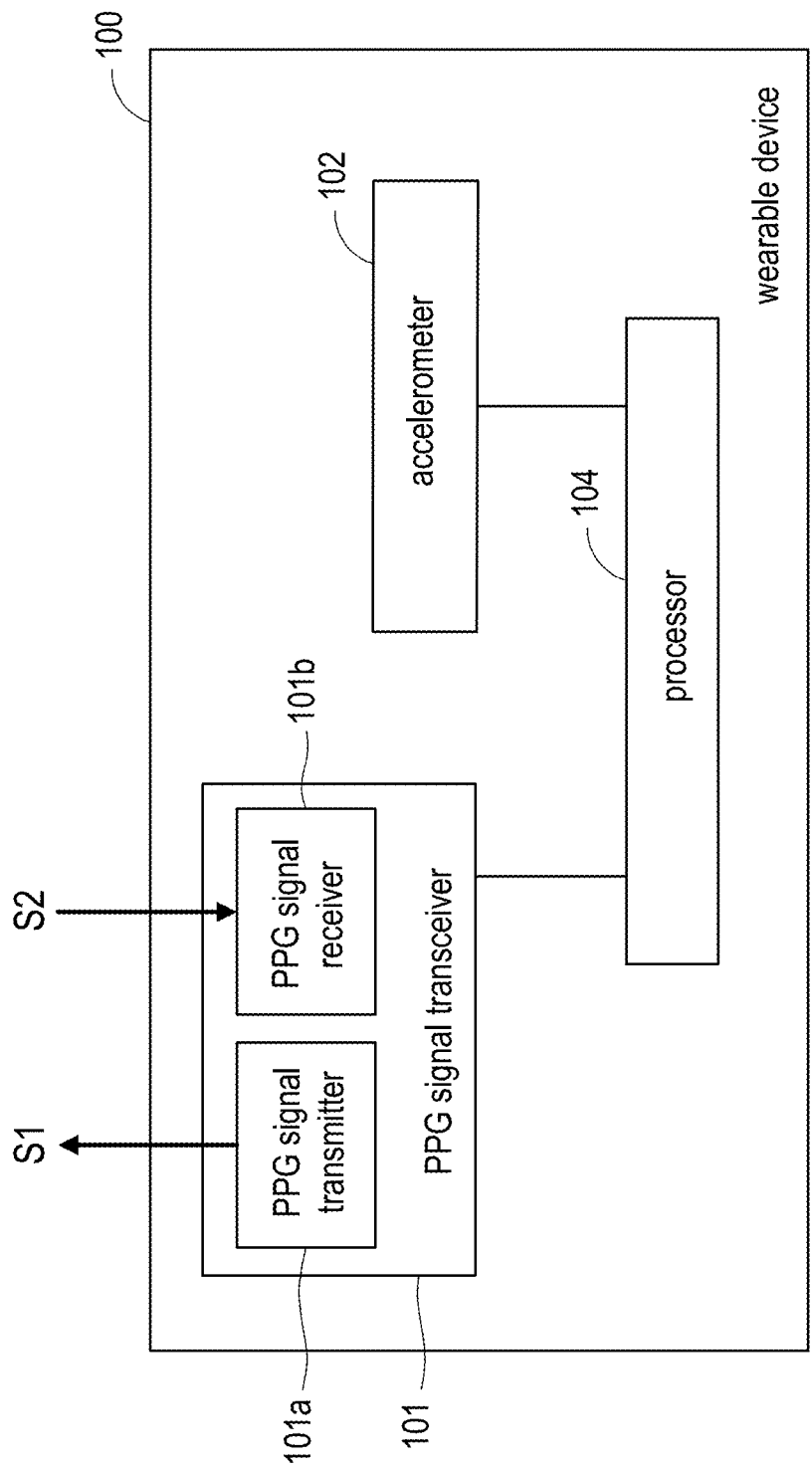
FIG. 1 is a schematic diagram of a wearable device according to an embodiment of the application.

Referring to FIG. 1, FIG. 1 is a schematic diagram of a wearable device according to an embodiment of the application. In FIG. 1, the wearable device 100 includes a photoplethysmography (PPG) signal transceiver 101, an accelerometer 102 and a processor 104. The PPG signal transceiver 101 and the accelerometer 102 are coupled to the processor 104.

In some embodiments, the PPG signal transceiver 101 may, for example, be placed on the wearable device 100 and on the contact surface of the user (or wearer). In an embodiment, the PPG signal transceiver 101 may, for example, include a PPG signal transmitter 101*a* and a PPG signal receiver 101*b*. The PPG signal transmitter 101*a* can be used to transmit PPG signals (it is generally green light), and these PPG signals can be received by the PPG signal receiver 101*b* after being reflected by some objects.

In an embodiment, when the wearable device 100 is being worn by the user, the PPG signals emitted by the PPG signal transmitter 101*a* can be reflected by the user's skin/subcutaneous tissue. Then, the reflected PPG signals can be received by the PPG signal receiver 101*b*.

In an embodiment, human blood vessels and blood flow will change according to the heartbeat, showing conditions such as dilation and constriction of blood vessels. In this case, after the PPG signal is irradiated on the blood vessel of the user and reflected, the intensity of the reflected PPG signal received by the PPG signal receiver 101*b* may also show a corresponding change. Based on this, the processor 104 can estimate the user's heart rate based on the change in the intensity of the PPG signal received by the PPG signal receiver 101*b*.

Figure 2:
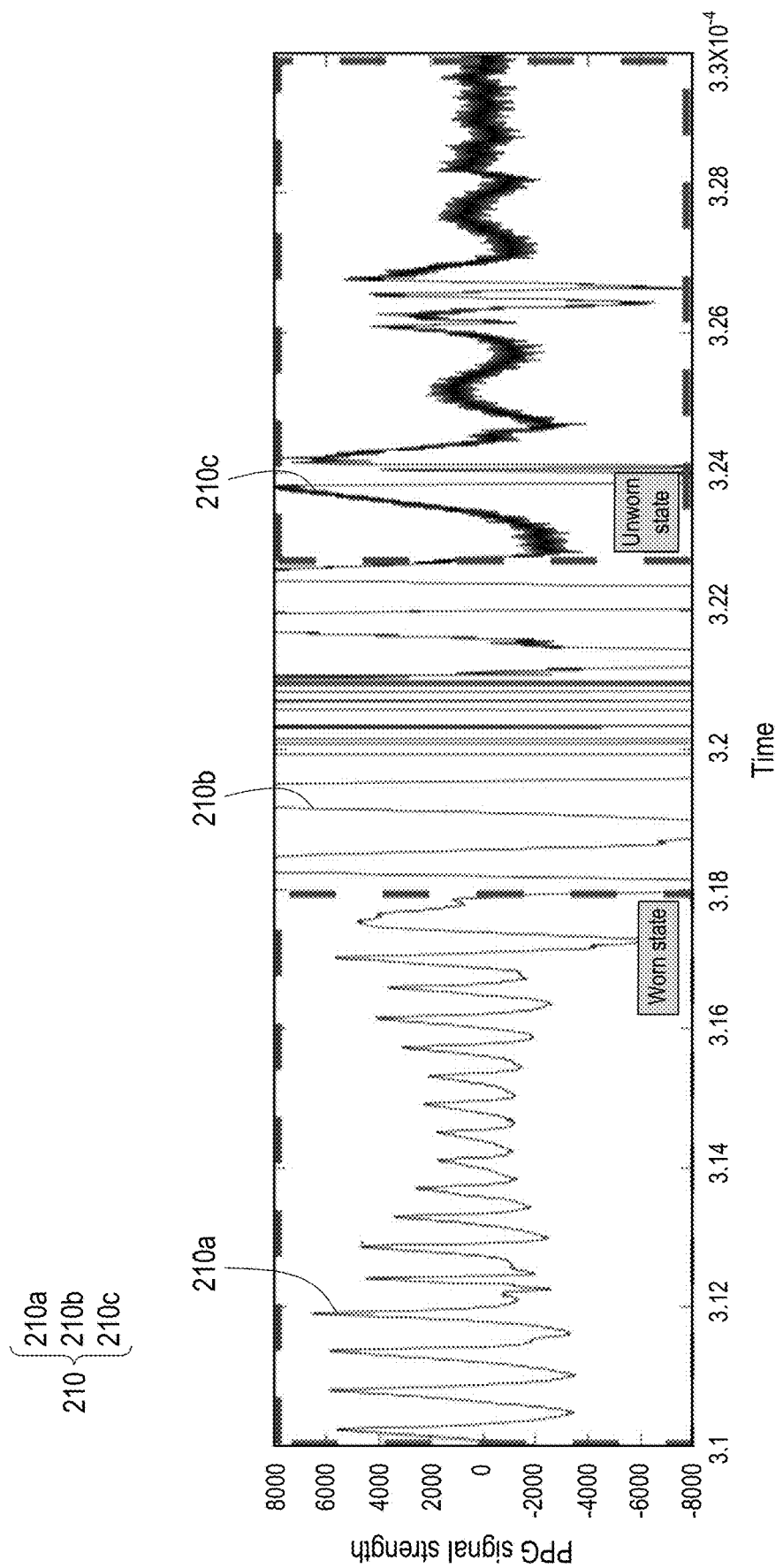
FIG. 2 is a schematic diagram of PPG signal changes according to FIG. 1.

Referring to FIG. 2, FIG. 2 is a schematic diagram of PPG signal changes according to FIG. 1. In FIG. 2, the PPG signal waveform 210 may include waveforms 210*a*, 210*b*, and 210*c*. The waveform 210*a* is, for example, the PPG signal change when the wearable device 100 is in a worn state (that is, the wearable device 100 is being worn on the user), the waveform 210b is, for example, the PPG signal change in the process of the user taking off the wearable device 100, and the waveform 210c is, for example, the PPG signal change when the wearable device 100 is in an unworn state (such as the wearable device 100 is taken off and placed somewhere).

As shown in the waveform 210a of FIG. 2, when the wearable device 100 is in the worn state, the PPG signal may show a corresponding change in response to the user's heart rate. At this time, since the signal received by the PPG signal receiver 101b has a lower frequency and less noise, the waveform of the PPG signal is also cleaner. In this case, the processor 104 can estimate the user's heart rate according to the waveform 210a.

When the wearable device 100 is being taken off, since the signal components received by the PPG signal receiver 101b are more complex (may include PPG signals reflected by users and other objects), the PPG signal changes drastically and unstable, as shown by the waveform 210b.

When the wearable device 100 is in the unworn state, since the PPG signal received by the PPG signal receiver 101b may contain more noise, the PPG signal may change at a higher frequency and may be unstable, as shown by the waveform 210c.

In some embodiments, the accelerometer 102 may be used, for example, to detect acceleration values of the wearable device 100 on multiple axes, and these acceleration values may change in response to the movement of the wearable device 100. Therefore, the processor 104 can determine whether the wearable device 100 is in a static state or a mobile state according to the acceleration value provided by the accelerometer 102.

In an embodiment, the processor 104 may determine the mobile energy parameter of the wearable device 100 after obtaining the acceleration value from the accelerometer 102, and determine whether the mobile energy parameter is less than an energy threshold. In an embodiment, the processor 104 may estimate the corresponding activity count as the mobile energy parameter of the wearable device 100 based on the acceleration value, but it may not be limited thereto.

In an embodiment, in response to determining that the mobile energy parameter is not greater than the energy threshold, the processor 104 may determine that the wearable device 100 is in the static state. On the other hand, in response to determining that the mobile energy parameter is greater than the energy threshold, the processor 104 may determine that the wearable device 100 is in a mobile state.

Figure 3:
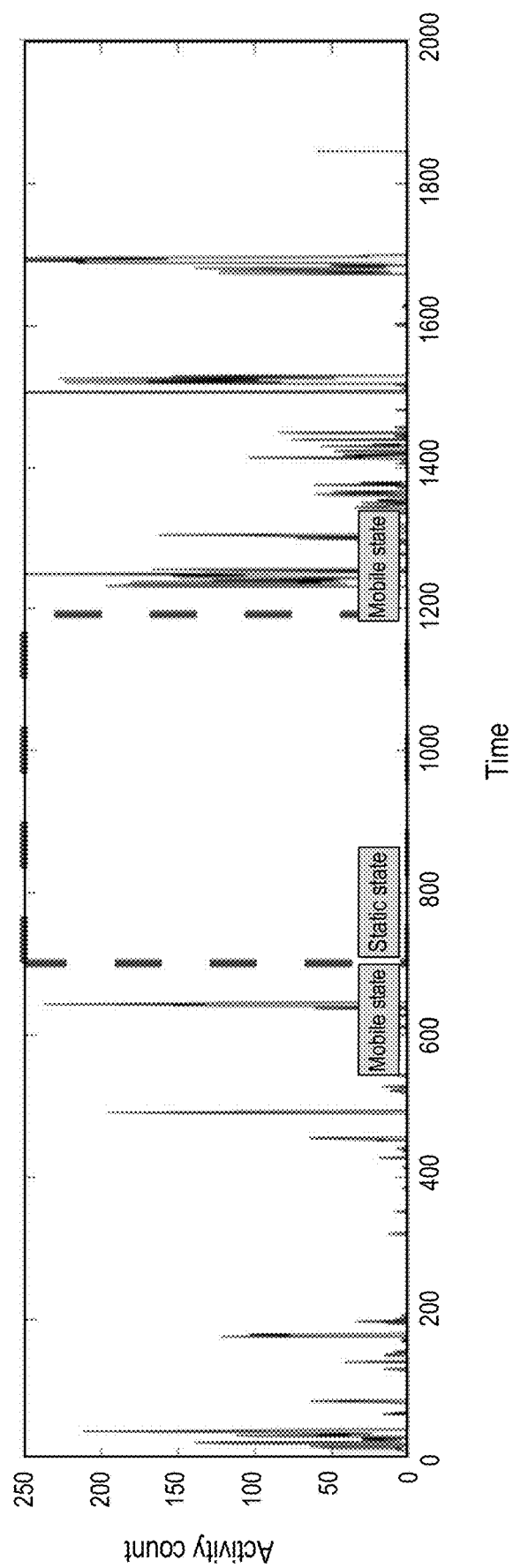
FIG. 3 is a diagram showing changes in activity counts according to an embodiment of the application.

Referring to FIG. 3, FIG. 3 is a diagram showing changes in activity counts according to an embodiment of the application. It can be seen from FIG. 3 that when the wearable device 100 is in the static state, its corresponding activity count may be in a state not greater than the energy threshold (for example, 0) for a long time. Therefore, the processor 104 can correspondingly determine that the wearable device 100 is in the static state, but it may not be limited to this.

In an embodiment of the present invention, the processor 104 can access specific modules and program to implement the wearing detection method proposed by the application.

Referring to FIG. 4, FIG. 4 is a flowchart of a wearing detection method according to an embodiment of the application. The method of this embodiment can be executed by the wearable device 100 of FIG. 1. The details of each step in FIG. 4 may be described below with the components shown in FIG. 1.

First, in Step S410, in response to determining that the wearable device 100 is in the static state, the processor 104 controls the PPG transceiver 101 to emit a plurality of first PPG signals S1 and detect a plurality of second PPG signals S2 corresponding to the first PPG signals S1. In an embodiment, the processor 104 may detect whether the wearable device 100 is in a static state based on the method mentioned in the description of FIG. 3, but it is not limited to this.

In an embodiment, after determining that the wearable device 100 is in the static state, the processor 104 may, for example, control the PPG signal transmitter 101a to transmit the first PPG signal S1 and control the PPG signal receiver 101b to receive the second PPG signals S2. The second PPG signal S2 is, for example, the PPG signal formed by the reflection of the first PPG signal S1. If it is determined that the wearable device 100 is in the static state, and the PPG signal transmitter 101a is in a state of continuously transmitting PPG signals, part of the PPG signals in the continuously transmitted PPG signals may be used as the first PPG signal S1. If it is determined that the wearable device 100 is in the static state, and the PPG signal transmitter 101a is in a state where it does not transmit PPG signals, then the PPG signal transmitter 101a is controlled to transmit the first PPG signal S1.

In an embodiment, suppose the processor 104 determines that the wearable device 100 is in the static state at the ith time point, the processor 104 may control PPG signal receiver 101b to detect multiple PPG signals between the i+Nth time point and the i+N+Mth time point as the second PPG signals S2, where i is an index value, and N and M are integers.

In different embodiments, the values of M and N can be determined according to the designer's needs. In an embodiment, when N is 0 and M is a positive integer, the processor 104 can understand that after determining that the wearable device 100 is in the static state, it immediately controls the PPG signal receiver 101b to detect multiple PPG signals between the ith time point and the i+Mth time point as the second PPG signal S2. In an embodiment, suppose the value of M is chosen to correspond to 2 seconds, the operation can be understood as immediately controlling the PPG signal receiver 101b to detect multiple PPG signals within 2 seconds as the second PPG signals S2 after determining that the wearable device 100 is in the static state.

In some embodiments, limited by the hardware characteristics of the PPG signal transceiver 101, if the PPG signals are detected immediately after it is determined that the wearable device 100 is in the static state (that is, the case where N is 0), the measured PPG signals may be unstable, thereby affecting the subsequent determination.

Therefore, in some embodiments, N and M can be set to positive integers. When both N and M are positive integers, the processor 104 may understand that after determining that the wearable device 100 is in the static state, it may wait for N time points and then control the PPG signal receiver 101b to detect a plurality of PPG signals between the i+Nth time point and the i+N+Mth time point as the second PPG signals S2. In one embodiment, suppose the values of N and M are chosen to correspond to 3 seconds and 2 seconds, respectively, the operation can be understood as, after determining that the wearable device 100 is in a static state, it may wait for 3 seconds and then control the PPG signal receiver 101b to detect multiple PPG signals within 2 seconds as the second PPG signal S2, but not limited to this.

Then, in Step S420, the processor 104 obtains the zero-crossing rate corresponding to the plurality of second PPG signals S2.

Figure 5A:
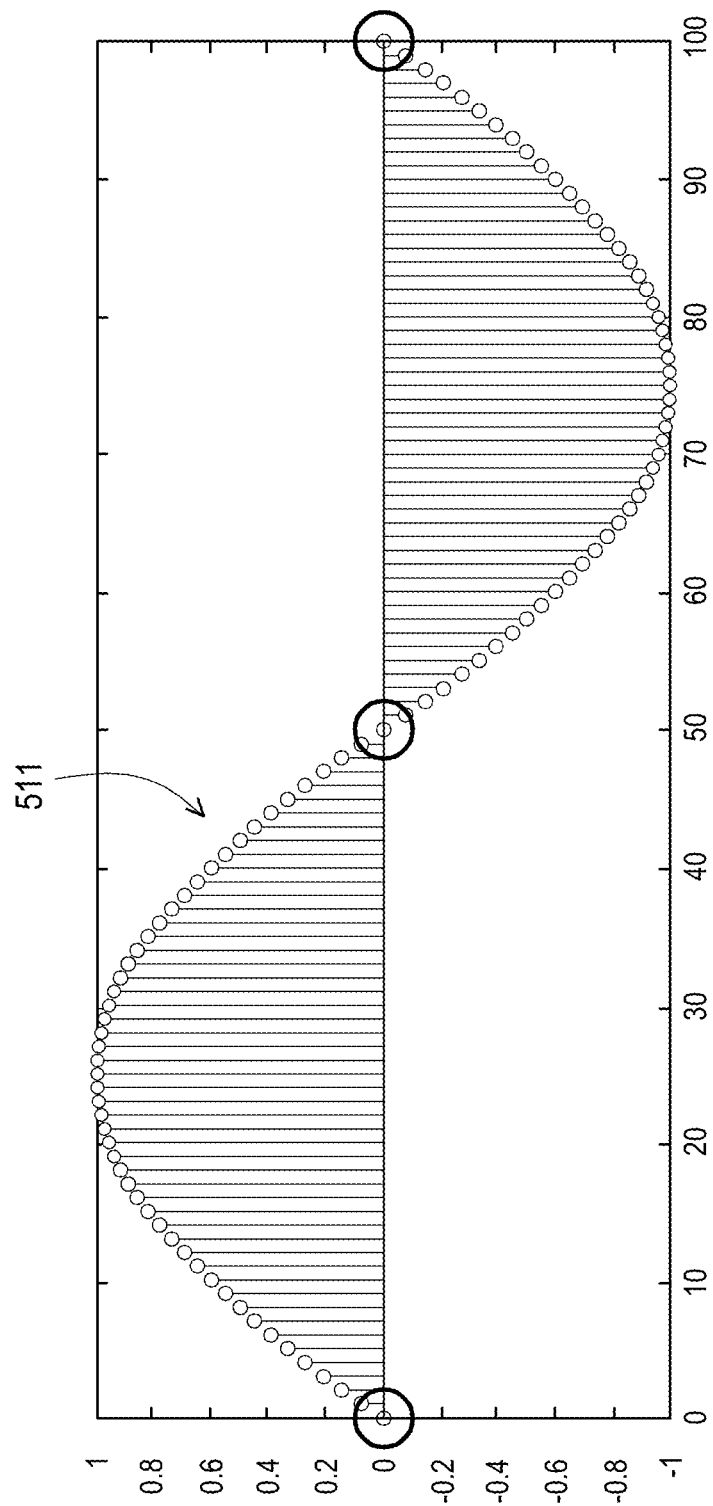
FIGS. 5A and 5B are schematic diagrams of estimating the zero-crossing rate of a signal according to an embodiment of the application.
Figure 5B:
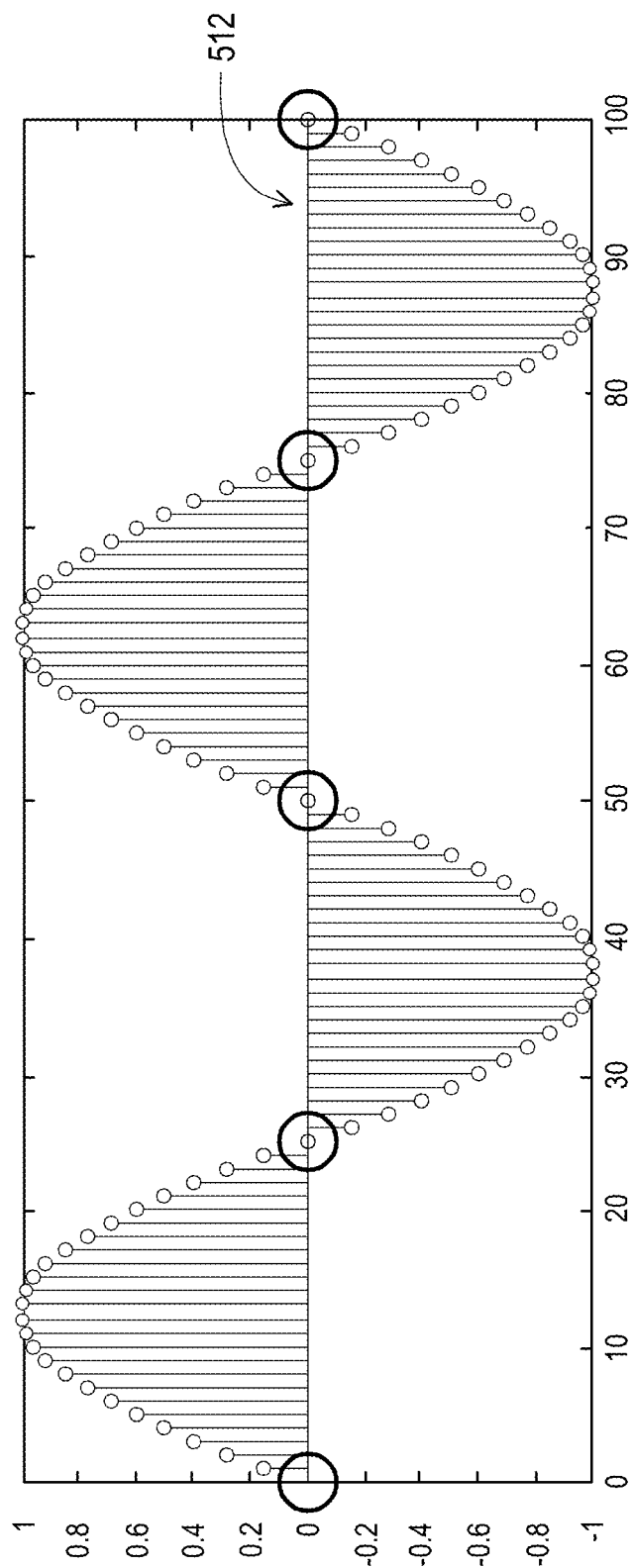

Referring to FIGS. 5A and 5B, FIGS. 5A and 5B are schematic diagrams of estimating the zero-crossing rate of a signal according to an embodiment of the application. In FIG. 5A, it is assumed that a certain signal A with a length of 1 second and a frequency (represented by $f_A$) of 1 exhibits a waveform 511 after sampling at a sampling frequency (represented by $f_s$) of 100 Hz. It can be seen from the waveform 511 that among the 100 points sampled, there are 3 zero-crossing points (that is, the circled points). Therefore, in the scenario of FIG. 5A, the zero-crossing rate of signal A can be estimated to be 3/100, that is $$\frac{2f_A + 1}{f_s}.$$

Besides, in FIG. 5B, it is assumed that a signal B with a length of 1 second and a frequency (represented by $f_B$) of 2 exhibits a waveform 512 after being sampled at a sampling frequency of 100 Hz. It can be seen from the waveform 512 that among the 100 points sampled, there are 5 zero-crossing points (that is, circled locations). Therefore, in the scenario of FIG. 5B, the zero-crossing rate of signal A can be estimated to be 5/100, that is $$\frac{2f_B + 1}{f_s}.$$

As can be seen from FIG. 5A and FIG. 5B, the processor 104 can estimate the zero-crossing rate of the signal based on the corresponding sampling frequency and the frequency of the signal after obtaining a signal. For example, the zero-crossing rate of a signal can be estimated as $$\frac{2f + 1}{f_s},$$

where f is the frequency of the signal, and $f_s$ is the sampling frequency used to sample the signal.

Based on this, in Step S420, the zero-crossing rate of the second PPG signal S2 can be estimated according to the principles after the processor 104 obtains the second PPG signal S2. In one embodiment, suppose the first frequency of the second PPG signal S2 is $f_1$ and the corresponding sampling frequency $f_s$, then the zero-crossing rate (represented by CR) of the second PPG signal S2 can be characterized as $$CR = \frac{2f_1 + 1}{f_s},$$

but not limited to this.

Then, in Step S430, the processor 104 determines whether the zero-crossing rates (CR) of the plurality of second PPG signals S2 are greater than the reference threshold value TH.

In an embodiment, the processor 104 may first execute a certain mechanism to determine the reference threshold TH. For example, the processor 104 may obtain the reference zero-crossing rate (represented by CR'), and correct the reference zero-crossing rate to the reference threshold value TH based on the correction factor.

In an embodiment, the processor 104 may first obtain a plurality of historical PPG signals in the process of obtaining the reference zero-crossing rate and estimate the reference zero-crossing rate based on the sampling frequency (that is, $f_s$) and the second frequency (represented by $f_2$) of these historical PPG signals, and the historical PPG signal is obtained when the wearable device 100 is in the worn state. In one embodiment, the reference zero-crossing rate CR' can be characterized, for example, as $$CR' = \frac{2f_2 + 1}{f_s}.$$

In addition, when the wearable device 100 is in the worn state, the PPG signal (i.e., historical PPG signal) received by the PPG signal receiver 101b may correspond to the user's heart rate as previously mentioned. Therefore, in one embodiment, the second frequency ($f_2$) of the historical PPG signal can also be expressed as HR/60, where HR is, for example, the heart rate of the user, and the unit is, for example, the number of times per minute (BPM). In this case, the reference zero-crossing rate CR' can, for example, be characterized as $$CR' = \frac{2(HR/60) + 1}{f_s}.$$

In some embodiments, the HR may be the average heart rate of the user within a certain period of time, for example, the average heart rate of the user in n seconds before the wearable device 100 is in the static state, but it is not limited thereto.

In some embodiments, the processor 104 may correct this reference zero-crossing rate to the reference threshold TH based on some correction factor after obtaining the reference zero-crossing rate CR'. In one embodiment, the correction factor may be selected to be a value greater than 1, but not limited thereto. In other words, the processor 104 may use a value greater than the reference zero-crossing rate as the reference threshold value TH. Due to the wide distribution of individual heart rhythms, for example, the resting heart rate can be as low as about 50 BPM, while the heart rate during exercise can be as high as about 200 BPM. In addition, different users may have different heart rate zones, and the resting heart rate and maximum heart rate may also be different. Therefore, if the reference threshold value TH is designed to be a certain value, misjudgment may occur among different users. The parameter HR in the reference threshold TH in this embodiment is the heart rate of the user, which means that the reference threshold TH may be adjusted according to the user's heart rate, such that different users may have different reference thresholds TH, which can reduce the occurrence of misjudgments. The parameter HR in the reference threshold TH in another embodiment of the application may be the real-time personal heart rate of the user before taking off the watch. For example, the average value of the inner heart rate for n seconds before the wearable device 100 is in the static state. Therefore, there may be a different reference threshold value TH according to the current heart rate of the user, which can more accurately determine whether the zero-crossing rate exceeds the real-time reference threshold value TH, and further determine whether the user indeed takes off the watch, thereby greatly reducing the occurrence of misjudgments.

In an embodiment, if the processor 104 determines that the zero-crossing rate of the second PPG signal S2 is greater than the reference threshold TH in step S430, the processor 104 may continue to perform step S440 to determine that the wearable device 100 is in the unworn state.

Specifically, as previously mentioned, when the wearable device 100 is not worn, the PPG signal receiver 101b may receive a PPG signal with a higher frequency, and the PPG signal with a higher frequency may have a correspondingly higher zero-crossing rate. Therefore, when the processor 104 determines that the zero-crossing rate of the second PPG signal S2 is greater than the set reference threshold value TH, the processor 104 can accordingly determine that the wearable device 100 should be in the unworn state.

Figure 6:
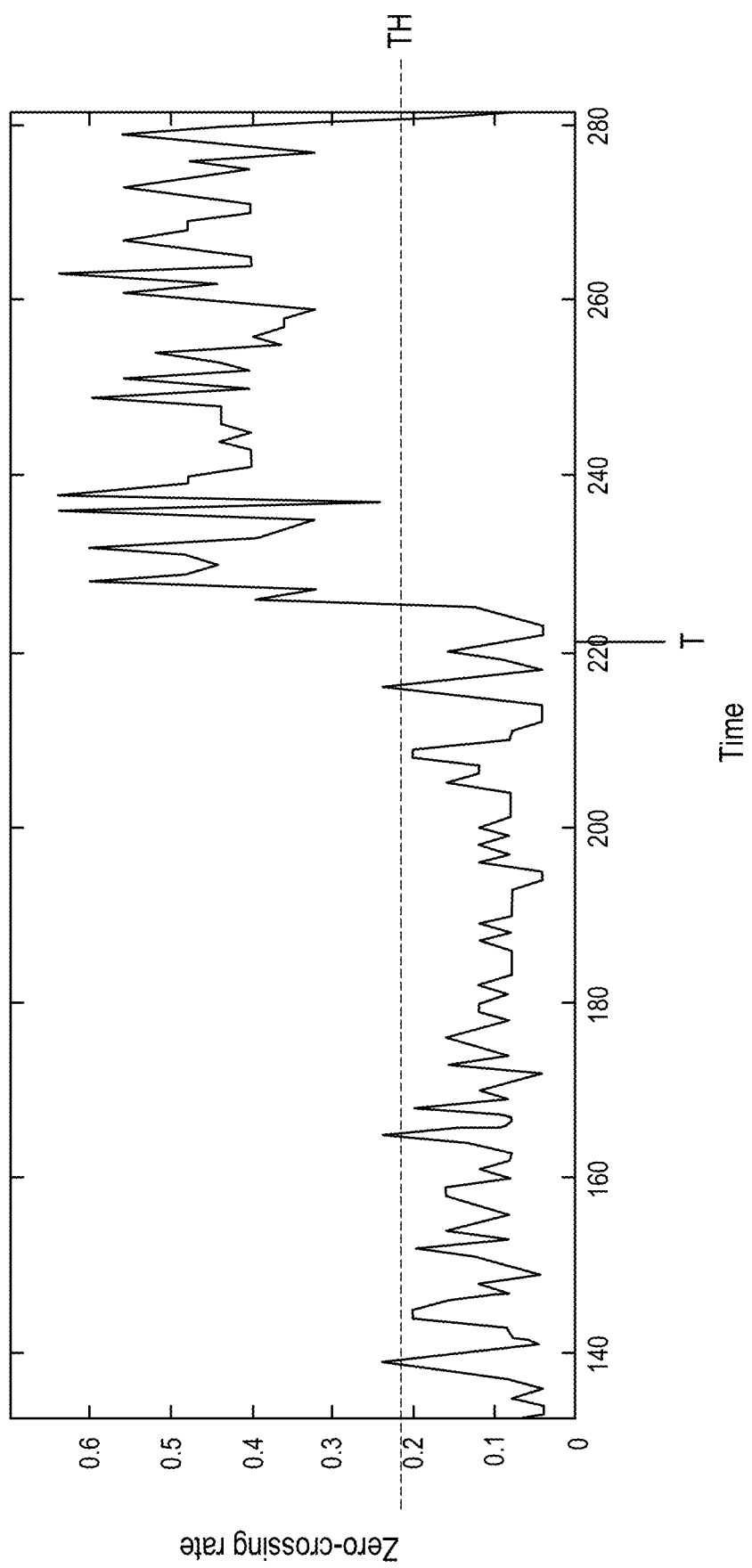
FIG. 6 is a diagram showing the zero-crossing rate change of the PPG signal according to an embodiment of the application.

Referring to FIG. 6, FIG. 6 is a diagram showing the zero-crossing rate change of the PPG signal according to an embodiment of the application. In FIG. 6, it is assumed that the wearable device 100 is in the worn state (e.g., worn on the user) before the time point T, and the wearable device 100 changes to the unworn state (e.g., taken off and placed somewhere) after the time point T. It can be seen in FIG. 6 that the zero-crossing rate of the PPG signal between the time points T is low, while the zero-crossing rate of the PPG signal after the time point T is high.

In an embodiment, the processor 104 may determine that the wearable device 100 is in the worn state before the time point T based on the previously taught mechanism. In this case, the processor 104 can obtain the partial PPG signal (such as, the partial PPG signal before time point T) when the wearable device 100 is in the worn state as the historical PPG signal to estimate the reference zero-crossing rate CR' and the corresponding reference threshold value TH.

In an embodiment, when the processor 104 detects that the wearable device 100 is in the static state at the time point T, the processor 104 can detect the required second PPG signal S2 based on the previous teaching. In the scenario of FIG. 6, the processor 104 may use a portion of the PPG signal measured after the time point T as the second PPG signal S2 considered, and estimate its zero-crossing rate accordingly.

In FIG. 6, after determining that the zero-crossing rate of the second PPG signal S2 under consideration is higher than the reference threshold value TH, the processor 104 can correspondingly determine that the wearable device 100 should be in the unworn state at this time. In this way, the wearable device 100 can achieve the technical effect of detecting whether the wearable device 100 is worn without being provided with a proximity sensor dedicated to detecting the human body.

Figure 7:
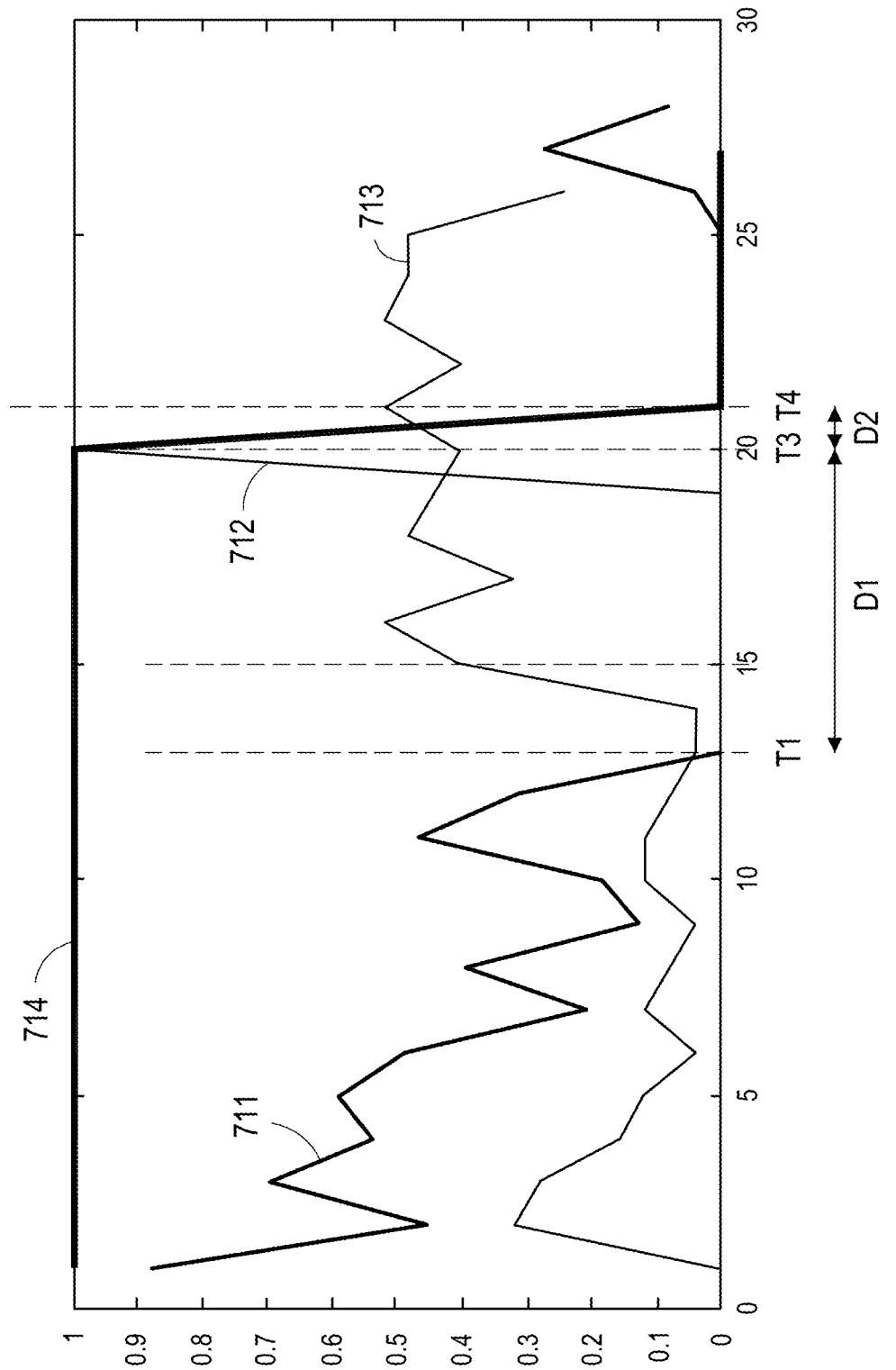
FIG. 7 is a diagram illustrating various waveforms according to an embodiment of the application.

Referring to FIG. 7, FIG. 7 is a diagram of various waveforms drawn according to an embodiment of the application. In FIG. 7, the waveform 711 corresponds, for example, to the movement energy parameter change of the wearable device 100, the waveform 712 corresponds, for example, to the enable signal change of PPG signal receiver 101b, the waveform 713 corresponds, for example, to the zero-crossing rate change of the PPG signal, and the waveform 714 corresponds to, for example, whether the wearable device 100 is in the worn state.

It can be seen from the waveform 711 that before the time point T1, the mobile energy parameters of the wearable device 100 are all greater than 0, that is, the wearable device 100 is in a non-static state before the time point T1. In this case, the waveform 714 may be at a high level corresponding to, for example, to indicate that the wearable device 100 is in the worn state.

In addition, it can also be seen from the waveform 711 that the movement energy parameter of the wearable device 100 becomes 0 at the time point T1, so the processor 104 can determine that the wearable device 100 is in a static state at the time point T1. After that, the processor 104 may receive the PPG signal through the PPG signal receiver 101b at the time point T3 after waiting for the time D1 corresponding to the N value.

In an embodiment, the PPG signal receiver 101b may detect the PPG signal within the time D2 (the length of which may correspond to the M value) after the time point T3 as the second PPG signal S2. In another embodiment, if the PPG signal transmitter 101a and the receiver 101b are disabled at the time point T1, the processor 104 can transmit an enable signal to the PPG signal transmitter 101a and the receiver 101b at the time point T3 after waiting for the time D1 corresponding to the value of N to enable the PPG signal transmitter 101a to transmit the PPG signal and the receiver 101b to receive the PPG signal. After the time point T3, the PPG signal within the time D2 (the length of which may correspond to the M value) is detected as the second PPG signal S2.

In FIG. 7, suppose that the zero-crossing rate of the second PPG signal S2 under consideration is determined to be greater than the reference threshold value, the processor 104 may determine that the wearable device 100 is in the unworn state at the time point T4, and the waveform 714 can be switched low accordingly to indicate that the wearable device 100 is in the unworn state, but not limited to this.

In an embodiment, after determining that the wearable device 100 is in the unworn state, the processor 104 may further control the PPG signal transceiver 101 to stop transmitting or receiving other PPG signals. Thereby, the effect of power saving can be further achieved. In another embodiment, the processor 104 can control the PPG signal transceiver 101 to transmit or receive other PPG signals only when the wearable device 100 changes to the mobile state, so as to detect whether the wearable device 100 changes to the worn state.

On the other hand, if the processor 104 determines that the zero-crossing rate of the second PPG signal S2 is not greater than the reference threshold TH in step S430, the processor 104 may continue to perform step S450 to determine that the wearable device 100 is in the worn state. In other words, the wearable device 100 may be in a static state because the user is in a relatively static posture (for example, watching TV, reading a book, sleeping, or other wearing hands in a static state) at this time, rather than being taken off to present the static state. In this case, the wearable device 100 can reduce the behavior of detecting whether the wearable device 100 is in the unworn state by transmitting/receiving the PPG signal, thereby achieving the effect of power saving. In short, if the processor 104 has previously determined that the wearable device 100 is in the static state and the worn state at the same time and the wearable device 100 is continuously in the static state, the processor 104 can wait a longer time to control the PPG signal transmitter 101a and the receiver 101b to transmit and detect the PPG signal when it is determined that the wearable device 100 is in the static state and needs to further determine whether it is in the worn state so as to achieve the effect of power saving. In another embodiment, the waiting time can be increased gradually. For example, the first waiting time is 3 seconds, the second waiting time is 30 seconds, and the third waiting time is 1 minute to achieve the effect of power saving. Moreover, in another embodiment, in this case, the wearable device 100 can further determine what state the user is in at this time, such as a sleep state. The PPG signal can be adjusted to transmit/receive to detect whether it is in the unworn state, which can also achieve the effect of power saving.

To sum up, in one embodiment, the processor 104 can achieve the power saving effect by increasing N. For ease of understanding, the increased N may be denoted by N' below. In detail, suppose the processor 104 determines that the wearable device 100 is in the static state at the jth (j is greater than i+N+M) time point, the processor 104 can control the PPG signal receiver 101b to detect a plurality of PPG signals between the j+N'th time point and the j+N'+Mth time point as PPG signals for determining whether the wearable device 100 is in the unworn state.

That is, the processor 104 waits for N' time points and then controls the PPG signal receiver 101b to detect multiple PPG signals between the j+N'th time point and the j+N'+M time point as PPG signals for determining whether the wearable device 100 is in the unworn state after determining that the wearable device 100 is in the static state at the jth time point.

On the contrary, if the processor 104 has previously determined that the wearable device 100 is in the mobile state and the non-worn state at the same time, and the wearable device 100 is continuously in the mobile state, for example, the wearable device 100 is placed in a mobile bag or in a vehicle, then, when the processor 104 determines that the wearable device 100 is in the mobile state next time and needs to further determine whether the wearable device 100 is in the worn state, after waiting for a long time, the PPG signal transmitter 101a and the receiver 101b are controlled to transmit and detect the PPG signal, thereby achieving the effect of power saving. The way of prolonging the waiting time can achieve the power saving effect by increasing N as described in the previous embodiment. Similarly, the waiting time can also be increased gradually to achieve the effect of saving power.

The application also provides a computer-readable storage medium for executing the wearing detection method. The computer-readable storage medium consists of a plurality of program instructions (e.g., setup, deployment program instructions). These program instructions can be loaded into the wearable device 100 for execution to perform the wear detection method and functions of the wearable device 100.

To sum up, the embodiment of the application can detect the PPG signals after it is determined that the wearable device is in the static state, and determine whether the wearable device is in the worn state or the unworn state based on the zero-crossing rate of the received PPG signals. In this way, the embodiments of the application can enable the wearable device to achieve the technical effect of detecting whether the wearable device is worn without being provided with a proximity sensor dedicated to detecting the human body. Thereby, the space of the wearable device can be used more efficiently, and the power consumption and the realization cost of the wearable device can be reduced at the same time.

Although the disclosure is described with reference to the above embodiments, the embodiments are not intended to limit the disclosure. A person skilled in the art may make variations and modifications without departing from the spirit and scope of the disclosure. Therefore, the protection scope of the disclosure should be subject to the appended claims.

What is claimed is:

1. A wearing detection method, comprising:
   in response to determining that the wearable device is in a static state, emitting a plurality of first photoplethysmography (PPG) signals, and detecting a plurality of second PPG signals corresponding to the first PPG signals;
   obtaining a zero-crossing rate corresponding to the second PPG signals;
   in response to determining that the zero-crossing rate of the second PPG signals is greater than a reference threshold, determining that the wearable device is in an unworn state;
   in response to determining that the zero-crossing rate of the second PPG signals is not greater than the reference threshold, determining that the wearable device is in a worn state.

2. The wearing detection method according to claim 1, further comprising:
   detecting multiple acceleration values of the wearable device through an accelerometer of the wearable device, and determining a mobile energy parameter of the wearable device accordingly;
   in response to determining that the mobile energy parameter is not greater than an energy threshold, determining that the wearable device is in the static state; and
   in response to determining that the mobile energy parameter is greater than an energy threshold, determining that the wearable device is in a mobile state.

3. The wearing detection method according to claim 1, wherein the step of detecting the second PPG signals corresponding to the first PPG signals comprises:
   in response to determining that the wearable device is in the static state at the ith time point, detecting multiple PPG signals between the i+Nth time point and the i+N+Mth time point as the second PPG signals, wherein i is an index value, and N and M are integers.

4. The wearing detection method according to claim 3, wherein after the step of determining that the wearable device is in the worn state, the method further comprises:
   increasing N.

5. The wearing detection method according to claim 1, wherein the step of obtaining the zero-crossing rate corresponding to the second PPG signals comprises:
   estimating the zero-crossing rate corresponding to the second PPG signals based on a sampling frequency and a first frequency of the second PPG signals.

6. The wearing detection method according to claim 5, wherein the zero-crossing rate corresponding to the second PPG signals is characterized as:

$$CR = \frac{2f_1 + 1}{f_s},$$

wherein $f_1$ is the first frequency of the PPG signal, and $f_s$ is the sample frequency.

7. The wearing detection method according to claim 1, further comprising:
   obtaining multiple historical PPG signals and estimating a reference zero-crossing rate based on the historical PPG signals, wherein the historical PPG signals are obtained when the wearable device is in the worn state; and
   correcting the reference zero-crossing rate to the reference threshold based on a correction factor.

8. The wearing detection method according to claim 1, wherein the reference threshold is adjusted according to the user's heart rate.

9. The wearing detection method according to claim 1, wherein after the step of determining that the wearable device is in the unworn state, the method further comprises:
stopping transmitting or receiving other PPG signals.

10. A wearable device, comprising:
a photoplethysmography (PPG) transceiver,
a processor, coupled to the PPG transceiver, wherein
in response to determining that the wearable device is in a static state by the processor, the processor controls the PPG transceiver to emit a plurality of first PPG signals and detect a plurality of second PPG signals corresponding to the first PPG signals;
a zero-crossing rate corresponding to the second PPG signals is obtained by the processor;
in response to determining that the zero-crossing rate of the second PPG signals is greater than a reference threshold by the processor, the processor determines that the wearable device is in an unworn state; and
in response to determining that the zero-crossing rate of the second PPG signals is not greater than the reference threshold, it is determined that the wearable device is in a worn state.

11. The wearable device according to claim 10, further comprising an accelerometer coupled to the processor for detecting multiple acceleration values of the wearable device, wherein the processor is configured to:
determine a mobile energy parameter of the wearable device according to the acceleration values;
in response to determining that the mobile energy parameter is not greater than an energy threshold, determine that the wearable device is in the static state; and
in response to determining that the mobile energy parameter is greater than an energy threshold, determine that the wearable device is in a mobile state.

12. The wearable device according to claim 10, wherein the processor is configured to:
in response to determining that the wearable device is in the static state at the ith time point, detect multiple PPG signals between the i+Nth time point and the i+N+Mth time point as the second PPG signals, wherein i is an index value, and N and M are integers.

13. The wearable device according to claim 12, wherein after determining that the wearable device is in the worn state, the processor is further configured to increase N.

14. The wearable device according to claim 10, wherein the processor is configured to:
estimate the zero-crossing rate corresponding to the second PPG signals based on a sampling frequency and a first frequency of the second PPG signals.

15. The wearable device according to claim 14, wherein the zero-crossing rate corresponding to the second PPG signals is characterized as:

$$CR = \frac{2f_1 + 1}{f_s},$$

wherein $f_1$ is the first frequency of the PPG signal, and $f_s$ is the sample frequency.

16. The wearable device according to claim 10, wherein the processor is configured to:
obtain multiple historical PPG signals and estimate a reference zero-crossing rate based on the historical PPG signals, wherein the historical PPG signals are obtained when the wearable device is in the worn state; and
correct the reference zero-crossing rate to the reference threshold based on a correction factor.

17. The wearable device according to claim 10, wherein the reference threshold is adjusted according to the user's heart rate.

18. The wearable device according to claim 10, wherein after determining that the wearable device is in the unworn state, the processor is further configured to:
control the PPG transceiver to stop transmitting or receiving other PPG signals.

19. A computer readable storage medium, wherein the computer readable storage medium records an executable computer program that is loaded by a wearable device to perform the following steps:
in response to determining that the wearable device is in a static state, emitting a plurality of first photoplethysmography (PPG) signals, and detecting a plurality of second PPG signals corresponding to the first PPG signals;
obtaining a zero-crossing rate corresponding to the second PPG signals;
in response to determining that the zero-crossing rate of the second PPG signals is higher than a reference threshold, determining that the wearable device is in an unworn state;
in response to determining that the zero-crossing rate of the second PPG signals is not greater than the reference threshold, determining that the wearable device is in a worn state.

* * * * *